United States Patent [19]
Aaslyng et al.

[11] Patent Number: 5,948,121
[45] Date of Patent: Sep. 7, 1999

[54] LACCASES WITH IMPROVED DYEING PROPERTIES

[75] Inventors: Dorrit Aaslyng, Værløse; Niels Henrik Sørensen, Skævinge; Karen Rørbæk, Veksø Sj., all of Denmark

[73] Assignee: Novo Nordisk A/S, Novo Alle, Denmark

[21] Appl. No.: 09/083,485

[22] Filed: May 22, 1998

Related U.S. Application Data

[63] Continuation of application No. PCT/DK96/00499, Nov. 29, 1996.

[30] Foreign Application Priority Data

Nov. 30, 1995 [DK] Denmark ........................ 1357/95

[51] Int. Cl.$^6$ .................... C09B 67/00; A61K 7/13
[52] U.S. Cl. .............. 8/401; 8/405; 8/406; 8/414; 8/415; 8/416; 8/421; 8/423; 8/424; 435/263; 435/189; 435/190; 435/191
[58] Field of Search ................ 8/401, 405, 406, 8/414, 415, 416, 421, 423, 424; 435/263, 189, 190, 191

[56] References Cited

U.S. PATENT DOCUMENTS

| | | | |
|---|---|---|---|
| 3,251,742 | 5/1966 | Soloway | 8/401 |
| 5,667,531 | 9/1997 | Yaver et al. | 8/401 |
| 5,750,388 | 5/1998 | Berka et al. | 435/189 |
| 5,795,760 | 8/1998 | Berka et al. | 435/189 |

FOREIGN PATENT DOCUMENTS

| | | |
|---|---|---|
| WO 94/00100 | 1/1994 | WIPO . |
| WO 95/07988 | 3/1995 | WIPO . |
| WO 95/33836 | 12/1995 | WIPO . |
| WO 95/33837 | 12/1995 | WIPO . |
| WO 96/00290 | 1/1996 | WIPO . |

OTHER PUBLICATIONS

Abstract–CAPLUS acceession No. 1991:498981, Saruno, Rinjiro: Hair dyeing preparations containing melanin or other polyphenol pigments and manufacture of the pigments; For JP 03077813 A2 910403.

Abstract–CAPLUS accession No. 1995: 974547, for Chivukula, Muralikrishna et al.: "Phenolic azo dye oxidation by laccase from *Pyricularia oryzae*"; Appl. Environ. Microbiol. (1995), 61(12), 4374–77. (Month Unknown).

*Primary Examiner*—Alan Diamond
*Attorney, Agent, or Firm*—Steve T. Zelson; Reza Green

[57] ABSTRACT

The present invention relates to a permanent dyeing composition comprising a) above 0 to 1 mg enzyme protein per ml dyeing composition of microbial laccase, b) one or more dye precursor, and c) optionally one or more dye modifiers, the use of the dyeing composition for dyeing keratinous fibers, such as hair, fur, hide, and wool, and a method for permanent dyeing of keratinous fibers.

13 Claims, 4 Drawing Sheets

LACCASES WITH IMPROVED DYEING PROPERTIES

CROSS-REFERENCE TO RELATED APPLICATIONS

This application is a continuation of application Ser. No. PCT/DK96/00499 filed on Nov. 29, 1996 and claims priority under 35 U.S.C. 119 of Danish application 1357/95 filed on Nov. 30, 1995, the contents of which are fully incorporated herein by reference.

FIELD OF THE INVENTION

The present invention relates to a dyeing composition comprising a microbial laccase, the use of said dyeing composition for dyeing keratinous fibres, in particular hair, fur, hide and wool, and a method for dyeing keratinous fibres.

BACKGROUND OF THE INVENTION

It has been used for many years to dye the hair to cover appearing grey hair. The need to do so arises from the fact that grey hair is the first sign of having past adolescence, which can be hard to accept for many people.

For instance, in certain parts of Asia it is widely used by both men and women to dye the hair with dyes often referred to by humorous people as "black shoe polish".

During the last few decades hair dyeing has become more and more popular in the western world. At first Punk Rockers and other society critical groups dyed their hair in extreme colours as a part of their protest against the established society, but today especially many young people also uses hair dyes (in more soft tints than the Punk Rockers) as a sort of "cosmetic" to change or freshen up their "look". Hair dyes In general hair dyeing compositions on the market today can be divided into three main groups:
temporary hair dyes,
semi-permanent hair dyes, and
permanent oxidative hair dyes.

The temporary hair dyes are only intended to change the natural hair colour for a short period of time and usually functions by depositing dyes on the surface of the hair. Such hair dyes are easy to remove with normal shampooing.

When using semi-permanent hair dyes the colour of the dyed hair can survive for five or more shampooings. This is achieved by using dyes having a high affinity for hair keratin and which is able penetrate into the interior of the hair shaft.

Permanent hair dyes are very durable to sunlight, shampooing and other hair treatments and need only to be refreshed once a month as new hair grows out. With these dyeing systems the dyes are created directly in and on the hair. Small aromatic colourless dye precursors (e.g. p-phenylene-diamine and o-aminophenol) penetrate deep into the hair where said dye precursors are oxidised by an oxidising agent into coloured polymeric compounds. These coloured compounds are larger than the dye precursors and can not be washed out of the hair.

By including compounds referred to as modifiers (or couplers) in the hair dyeing composition a number of hair colour tints can be obtained. Cathecol and Resorcinol are examples of such modifiers.

Traditionally $H_2O_2$ is used as the oxidizing agent (colour builder), but also as a bleaching agent. Dyeing compositions comprising $H_2O_2$ are often referred to as "lightening dyes" due to this lightening effect of $H_2O_2$.

The use of $H_2O_2$ in dyeing compositions have some disadvantages as $H_2O_2$ damages the hair. Further, oxidative dyeing often demands high pH (normally around pH 9–10), which also inflicts damage on the hair and on the skin. Consequently, if using dye compositions comprising $H_2O_2$ it is not recommendable to dye the hair often. To overcome the disadvantages of using $H_2O_2$ it has been suggested to use oxidation enzymes to replace $H_2O_2$.

U.S. Pat. No. 3,251,742 (Revlon) describes a method for dyeing human hair by dye formation in situ (i.e. on the hair). An oxidative enzyme is used to the colour formation reactions at a substantially neutral pH (7–8.5). Laccases, tyrosinases, polyphenolases and catacolases are mentioned as suitable oxidation enzymes. The only exemplified oxidation enzyme is tyrosinase.

EP patent no. 504.005 (Perma S.A.) concerns dyeing compositions for keratinous fibres, in particular hair, which do not require the presence of $H_2O_2$ (hydrogen peroxide). The composition comprises an enzyme capable of catalysing the formation of the polymeric dyes and also dye precursors, such as bases and couplers, in a buffer solution wherein the pH of said composition is between 6.5 and 8 and said enzyme has an optimal activity in the pH range between 6.5 and 8.

*Rhizoctonia praticola* laccase and *Rhus vernicifera* laccase are the only laccases exemplified in the patent.

Abstract of Papers American Chemical Society vol. 209, no. 1–2, 1995 discloses the cloning of laccases from *Scytalidium thermophilum* and *Myceliophthora thermophila*. The abstract does not mention the use of said laccases for dyeing.

SUMMARY OF THE INVENTION

The object of the present invention is to provide improved dyeing compositions for keratinous fibres, such as hair, fur hide and wool, comprising an oxidative enzyme as the oxidising agent.

In the context of the present invention an "improved" composition for dyeing keratinous fibres means a composition being capable of dyeing the keratinous fibres in question faster or by the use of a smaller amount of oxidation enzyme to obtain an optimal dyeing effect, determined as $\Delta E^*$, in comparison to corresponding prior art dyeing compositions.

Further, it is also possible to use a less amount of dye precursor. This is advantageous as certain dye precursors are very unhealthy and very carcinogenic.

Compositions capable of dyeing the keratinous fibres, in particular hair, fur, hide and wool, faster are desirable as such compositions are very user convenient.

Further, it is desirable to be able to use a less amount of enzyme in the dyeing composition. This might make the dyeing process more economical. Further, the risk for creating airborne protein aerosols is reduced.

It has now surprisingly been found that it is possible to provide such improved dyeing compositions for keratinous fibres by using microbial laccases for oxidising the dye precursor(s).

Laccases (benzenediol:oxygen oxidoreductases) (E.C. class 1.10.3.2 according to Enzyme Nomenclature (1992) Academic Press, Inc.) are multi-copper containing enzymes that catalyse the oxidation of phenols. Laccase-mediated oxidation results in the production of aryloxy-radical intermediates from suitable phenolic substrates; the ultimate coupling of the intermediates so produced provides a combination of dimeric, oligomeric, and polymeric reaction products. Certain reaction products may be used to form dyes suitable for dyeing keratinous fibres, such as hair and wool (see below).

Firstly, the object of the invention is to provide a dyeing composition comprising
a) above 0 to 1 mg enzyme protein per ml dyeing composition of microbial laccase,
b) one or more dye precursors,
c) optionally one or more modifiers.

Specifically contemplated is laccases of microbial origin, derived from a strain of the genus Myceliophthora.

In the second aspect the invention relates to the use of a dyeing composition of the invention for dyeing keratinous fibres, such as hair, fur, hide and wool.

The invention also related to a method for dying keratinous fibres comprising contacting the dyeing composition of the invention to the keratinous fibres in question under suitable conditions and for a period of time sufficient to permit oxidation of the dye precursor into a coloured compound.

The invention also relates to the use of a laccase for permanent dyeing of keratinous fibres wherein said laccase is a laccase that results in a $\Delta E^*$-value higher than the $\Delta E^*$-value resulting from a laccase derived from Rhus under corresponding dyeing conditions.

This means that when dyeing keratinous fibres with a dyeing composition of the present invention the $\Delta E^*$-value determined are higher than the $\Delta E^*$-value determined from corresponding keratinous fibres dyed under the same conditions using a dyeing composition comprising a laccase derived from Rhus.

The term "corresponding dyeing conditions" means under conditions where e.g. the enzyme concentration or enzyme activity, dyeing incubations time, dyeing incubation temperature, pH conditions, keratin fibre type (such as hair type) are the same, and further that the same dye precursor (s) and modifier(s) are used. In other words it defines conditions parallel to the specific dyeing conditions chosen. The dyeing conditions described below in the Examples may be chosen.

In the context of the present invention a "higher" $\Delta E^*$ value defines that the total quantitative colour change is more than one $\Delta E^*$ unit.

$\Delta E^*$ is calculated from the values of the parameters $a^*$, $b^*$ and $L^*$ determined e.g. on a Minolta CR200 Chroma Meter using the formula $\Delta E^* = \sqrt{(\Delta L^{*2} + \Delta a^{*2} + \Delta b^{*2})}$. The meaning of $a^*$, $b^*$ and $L^*$ is explained below in the "Materials and Methods" section.

DETAILED DESCRIPTION OF THE INVENTION

Figure 1:
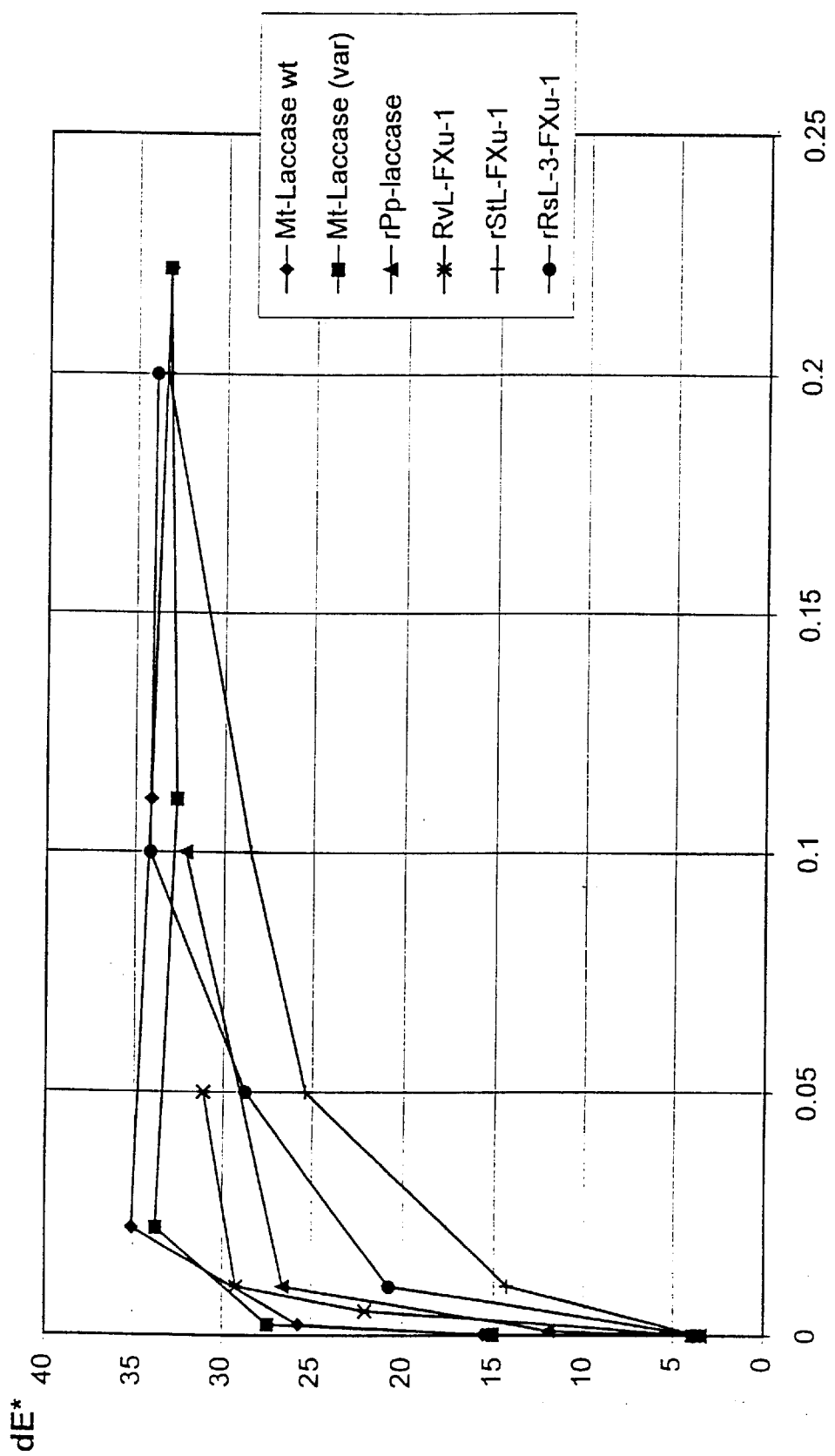
FIG. 1 shows the dyeing effect of six different laccases. The six laccases are the *Polyporus pinsitus* accase (rPp-laccase), *Myceliophthora thermophila* laccase (Mt-laccase wt.), *Myceliophthora thermophila* T1 variant laccase (Mt-laccase (var)), *Rhus vernicifera* laccase (Rvl-FXu-1), *Scytalidium thermophilum* laccase (rStL-FXu-1) and *Rhizoctonia solani* laccase (rRsL-3-FXu-1). o-aminophenol is used as the dye precursor and m-phenylene-diamine is used as a modifier.

The object of the present invention is to provide improved dyeing compositions for permanent dyeing of keratinous fibres, such as hair, fur, hide and wool, comprising an oxidation enzyme.

It has now surprisingly been found that it is possible to provide such improved dyeing compositions by using a microbial laccase for oxidising the dye precursor(s).

The Dyeing Composition

In the first aspect the present invention relates to a dyeing composition comprising
a) above 0 to 1 mg enzyme protein per ml dyeing composition of microbial laccase,
b) one or more dye precursor, and
c) optionally one or more dye modifiers.

In a preferred embodiment of the invention the laccase may be present in the dyeing compositions in a concentration within the range from 0.0001 to 1 mg/ml, preferably 0.001 to 0.8 mg/ml, more preferred 0.002 to 0.5, even more preferred 0.003 to 0.2, especially 0.004 to 0.1 mg enzyme protein/ml dyeing composition.

When dyeing with a composition of the invention for permanent dyeing the $\Delta E^*$-value obtained is higher than that obtained when using a dyeing composition comprising a laccase derived from Rhus under corresponding dyeing conditions.

An example of a Rhus laccase is the laccase derived from the Japanese varnish tree *Rhus vernicifera* (Yoshida, (1883), J. Chem. Soc., 472). The *Rhus vernicifera* laccase is used in the Example 1 below.

The microbial laccase used according to the invention is of fungal or bacteria origin, in particular of filamentous fungus origin.

In an embodiment of the invention the microbial laccase is derived from a strain of genus Myceliophthora, such as a strain of the species *Myceliophthora thermophila* e.g. the purified laccase described in WO 95/33836 (PCT/US95/06815) from Novo Nordisk, which is hereby incorporated by reference. SEQ ID NO 1 below shows a DNA sequence encoding a suitable laccase derivable from *Myceliophthora thermophila*.

*E. coli* JM101 containing the expression vector pRaMB5 comprising SEQ ID NO 1 has been deposited under the Budapest Treaty with the Agricultural Research Service Patent Culture Collection, Northern Regional Research Center, 1815 University Street, Peoria, Ill., 61604. The vector have been given the Accession Number NRRL B-21261.

Also contemplated according to the invention are laccases derived from other micro-organisms being more than 80% homologous to SEQ ID NO 1 derived from *Myceliophthora thermophila*.

In addition, Myceliophthora laccases also encompass alternative forms of laccases which may be found in *M. thermophila* and as well as laccases which may be found in other fungi which are synonyms that fall within the definition of *M. thermophila* as described by Apinis (Nova Hedwigia 5, 57–78, 1963) and named *Sporotrichum thermophile*. Subsequent taxonomic revisions have placed this organism in the genus Chysosporium (Von Klopotek, A. Arche., (1974) Microbiol, 98, 365–369) and later Myceliophthora (Van Oorshot, Persoonia, (1977), 9, 401–408). A number of organisms known by other names also appear to belong to this species. These include *Sporotrichum cellulophilum* (U.S. Pat. No. 4,106,989); *Thielavia thermophila*

(Fergus and Sinden (1968), Can. J. Botany, 47, 1635–1637); *Chrysosporium fergussi* and *Corynascus thermophilus* (Von Klopotek, supra).

Also the use of laccase variants are contemplated according to the present invention.

An example of a laccase variant is the *Myceliophthora thermophila* T1 variant described in PCT/US96/14087 (Novo Nordisk).

T1 variants (or Type I variants) are modified blue copper oxidases, including laccases. T1 variants can for instance be constructed by site-directed mutagenesis and differ from the corresponding wild-type blue copper oxidases by at least one amino acid residue in the Type I (T1) copper site. These modifications generally result in altered pH profiles and/or specific activity relatively to the wild-type enzymes. This can be advantageous when using the enzyme in question in dyeing compositions.

More specific the *Myceliophthora thermophila* T1 laccase variant may comprise the sequence 509VSGGL511 or may be modified as to increase the negative charge in at least one segment of the T1 copper site.

The above mentioned microbial laccases may advantageously be used in permanent dyeing composition for keratinous fibres. Such compositions have a superior dyeing effect to corresponding compositions comprising e.g. the *Rhus vernicifera* laccase as shown in Example 1.

The *Myceliophthora thermophila* T1 variant laccase is more wash stabile and further dyes faster than the *Polyporus pinsitus* laccase which is proven in Example 2 and Example 3, respectively.

Example 4 shows that less Myceliophthora laccase activity (i.e. LACU/ml) is needed to obtain a suitable dyeing effect in comparison to the *Polyporus pinsitus* laccase.

Example 5 shows that for the *Myceliophthora thermophila* laccase the dyeing effect optimum is obtained around 0.005 mg enzyme protein per ml dyeing composition.

In the case of using a Myceliophthora laccase in a permanent dyeing composition it may advantageously be present in concentrations from above 0 to 1 mg/ml, preferably 0.0001 to 0.1 mg/ml, more preferably 0.0005 to 0.05 mg/ml, especially 0.001 to 0.01 mg enzyme protein per ml dyeing composition.

It is to be understood that the laccase may be produced either homologously, or heterologously in a host cell such as filamentous fungus, yeast or bacteria.

Examples of filamentous fungi host cells include strains of the species of Trichoderma, preferably a strain of *Trichoderma harzianum* or *Trichoderma reesei,* or a species of Fusarium, or a species of Aspergillus, most preferably *Aspergillus oryzae* or *Aspergillus niger,* or yeast cells, such as e.g. a strain of Saccharomyces, in particular *Saccharomyces cerevisiae, Saccharomyces kluyveri* or *Saccharomyces uvarum,* a strain of Schizosaccharomyces sp., such as *Schizosaccharomyces pombe,* a strain of Hansenula sp., Pichia sp., Yarrowia sp., such as *Yarrowia lipolytica,* or Kluyveromyces sp., such as *Kluyveromyces lactis,* or a bacteria, such as gram-positive bacteria such as strains of Bacillus, such as strains of *B. subtilis, B. Licheniformis, B. lentus, B. brevis, B. stearothermophilus, B. alkalophilus, B. amyloliquefaciens, B. coagulans, B. circulans, B. lautus, B. megaterium* or *B. thuringiensis,* or strains of Streptomyces, such as *S. lividans* or *S. murinus,* or gram-negative bacteria such as *Escherichia coli.*

To obtain dyeing of the keratinous fibres the dyeing composition of the invention comprises one or more dye precursors which is(are) converted into coloured compound (s) by an oxidation agent which according to the present invention is a microbial laccase.

Without being limited thereto the dye precursor(s) may be (an) aromatic compound(s) belonging to one of three major chemical families: the diamines, aminophenols (or aminonaphtols) and the phenols. Examples of isatin derivative dye precursors can be found in DE 4,314,317-A1. Further, a number of indole or indoline derivative dye precursors are disclosed in WO 94/00100. Said dye precursors mentioned in these documents are hereby incorporated herein by reference.

Examples of suitable dye precursors include compounds from the group comprising p-phenylene-diamine (PPD), p-toluylene-diamine (PTD), chloro-p-phenylene-diamine, p-aminophenol, o-aminophenol, 3,4-diaminotoluene, 2-methyl-1,4-diaminobenzene, 4-methyl-o-phenylenediamine, 2-methoxy-p-phenylenediamine, 2-chloro-1,4-diamino-benzene, 4-amino diphenylamine, 1-amino-4-β-methoxyethylamino-benzene, 1-amino-4-bis-(β-hydroxyethyl)-amonibenzene, 1-3-diamino-benzene, 2-methyl-1,3-diamino-benzene, 2,4-diaminotoluene, 2,6-diaminopyridine, 1-hydroxy-2-amino-benzene, 1-hydroxy-3-amino-benzene, 1-methyl-2-hydroxy-4-amino-benzene, 1-methyl-2-hydroxy-4-β-hydroxyethylamino-benzene, 1-hydroxy-4-amino-ebnzene, 1-hydroxy-4-methylamino-benzene, 1-methoxy-2,4-diamino-benzene, 1-ethoxy-2,3-diamino-benzene, 1-β-hydroxyethyloxy-2,4-diamino-benzene, phenazines, such as 4,7-phenazinedicarboxylic acid, 2,7-phenazinedicarboxylic acid, 2-phenazinecarboxylic acid, 2,7-diaminophenazine, 2,8-diaminophenazine, 2,7-diamino-3,8-dimethoxyphenazine, 2,7-diamino-3-methoxyphenazine, 2,7-diamino 3-methoxyphenazine, 3-dimethyl 2,8-phenazinediamine, 2,2'-[(8-amino-7-methyl-2-phenazinyl)imino]bis-ethanol, 2,2'-[(8-amino-7-methoxy-2-phenazinyl)imino]bis-ethanol, 2,2'-[(8-amino-7-chloro-2-phenazinyl)imino]bis-ethanol, 2-[(8-amino-7-methyl-2-phenazinyl)amino]-ethanol, 2,2'-[(8-amino-2-phenazinyl)imino]bis-ethanol, 3-amino-7-(dimethylamino)-2,8-dimethyl-5-phenyl-chloride, 9-(diethylamino)- benzo[a]phenazine-1,5-diol, N-[8-(diethylamino)-2-phenazinyl]-methanesulfonamide, N-(8-methoxy-2-phenazinyl)- Methanesulfonamide, N,N,N', N'-tetramethyl-2,7-phenazinediamine, 3,7-dimethyl-2-phenazinamine, p-amino benzoic acids, such as p-amino benzoic acid ethyl, p-amino benzoic acid glycerid, p-amino benzoic acid isobutyl, p-dimethylamino benzoic acid amil, p-dimethylamino benzoic acid octyl, p-diethoxy amino benzoic amil, p-dipropoxy amino benzoic acid ethyl, acetylsalicylic acid, isatin derivatives, such as 2,3-diamino benzoic acid.

In an embodiment the laccase is used with the dye precursor directly to oxidise it into a coloured compound. The dye precursor may be used alone or in combination with other dye precursors.

It is believed that when using a diamine or an aminophenol as the dye precursor at least one of the intermediates in the co-polymerisation must be an ortho- or para-diamine or aminophenol. Examples of such are found below and are also described in U.S. Pat. No. 3,251,742 (Revlon), the contents of which are incorporated herein by reference.

Optionally dyeing compositions (especially hair dyeing compositions) of the invention also comprise a modifier (coupler) by which a number of colour tints can be obtained. In general modifiers are used in dyeing composition for hair as the hair colours resulting from hair dyeing compositions without modifier(s) are usually unacceptable for most people.

Modifiers are typically m-diamines, m-aminophenols, or polyphenols. Upon the optional addition of a modifier (coupler) it reacts with the dye precursor(s) in the presence of e.g. a laccase, converting the dye precursor(s) into a coloured compound.

Examples of modifiers (couplers) include m-phenylenediamine, 2,4-diaminoanisole, 1-hydroxynaphthalene($\alpha$-naphthol), 1,4-dihydroxybenzene(hydroquinone), 1,5-dihydroxynapthalene, 1,2-dihydroxybenzene(pyrocatechol), 1,3-dihydroxybenzene (resorcinol), 1,3-dihydroxy-2-methylbenzene, 1,3-dihydroxy-4-chlorobenzene(4-chlororesorcinol), 1,2,3,trihydroxybenzene, 1,2,4-trihydroxybenzene, 1,2,4-trihydroxy-5-methylbenzene, 1,2,4-trihydroxytoluene.

When using the dyeing compositions of the invention a reduced amount of enzyme (i.e. mg enzyme protein per ml dyeing composition) is needed to obtain the maximal dyeing effect (See FIG. 1 and FIG. 4), determined as the optimal $\Delta E^*$-value, in comparison to prior art dyeing compositions, such as dyeing compositions comprising a laccase derived from Rhus.

The amount of dye precursor(s) and other ingredients used in the composition of the invention are in accordance with usual commercial amounts.

According to the invention the product comprising the dyeing composition may be a one or a two compartment product. In the one compartment product the laccase, the dye precursor(s) and other ingredients are keep together in a stabilised solution or kept under stable conditions (i.e. the dye precursors are not oxidised by the laccase). In a two compartment product the laccase and the dye precursor(s) and other ingredients are keep in two containers keep apart. The contents of said containers are mixed immediately before use.

USE

In the second aspect the invention relates to the use of the dyeing composition of the invention for permanent dyeing of keratinous fibres, in particular hair, fur, hide and wool.

When using a dying composition of the invention the $\Delta E^*$-value obtained is higher than that of a dyeing composition comprising a laccase derived from genus Rhus under corresponding dyeing conditions (see FIG. 1).

Method

In the third aspect the invention relates to a method for permanent dying of keratinous fibres comprising contacting a dyeing composition of the invention with the keratinous fibres in question under suitable conditions and for a period of time sufficient to permit oxidation of the dye precursor into a coloured compound.

The dyeing procedure may be carried out at room temperature, preferably around the optimal temperature of the enzyme, typically with from 10 to 60° C.; at a pH in the range from 3 to 10, preferably 5 to 9, especially 6 to 8; for a period of time between 10 and 60 minutes, preferably 15 to 50 minutes, especially 20 to 40 minutes.

When using the method of the invention the $\Delta E^*$-value obtained is higher than that of corresponding methods where a laccase derived from a strain of the genus Rhus are used under the same dyeing conditions, in the presence or absence of at least one modifier, with at least one dye precursor, for a period of time, and under conditions sufficient to permit oxidation of the dye precursor used for oxidising the dye.

The method can be conducted with one or more dye precursors, either alone or in combination with one or more modifiers.

MATERIALS AND METHODS

Materials

Hair: 6" De Meo Virgin Natural White Hair (De Meo Brothers Inc. USA)

Enzymes:

*Myceliophthora thermophila* laccase described in WO 95/33836 (PCT/US95/06815) from Novo Nordisk Biotech, Inc.

*Myceliophthora thermophila* T1 variant laccase described in U.S. patent application 60/003,142 from Novo Nordisk Biotech, Inc.

*Polyporus pinsitus* laccase described in WO 96/00290 (PCT/US95/07536) from Novo Nordisk Biotech, Inc.

*Rhus vernicifera* laccase (Yoshida, J. Chem. Soc., 472 (1883) *Rhizoctonia solani* laccase described in WO 95/07988 from Novo Nordisk Biotech, Inc.

*Scytalidium thermophilum* laccase described in WO 95/33837 (PCT/US95/06816) from Novo Nordisk Biotech, Inc.

Deposit of Biological Material

The following biological material has been deposited on the May 25, 1994 under the terms of the Budapest Treaty with the Agricultural Research Service Patent Culture Collection, Northern Regional Research Center, 1815 University Street, Peoria, Ill., 61604 and given the following accession number.

| Deposit | Accession Number |
|---|---|
| *E. coli* JM101 containing pRaMB5 | NRRL B-21261 |

Dye precursors: 0.1% w/w p-phenylene-diamine in 0.1 M K-phosphate buffer, pH 7.0. (pPD) 0.1% w/w p-toluylene-diamine in 0.1 M K-phosphate buffer, pH 7.0. 0.1% w/w chloro-p-phenylenediamine in 0.1 M K-phosphate buffer, pH 7.0. 0.1% w/w p-aminophenol in 0.1 M K-phosphate buffer, pH 7.0. 0.1% w/w o-aminophenol in 0.1 M K-phosphate buffer, pH 7.0. 0.1% w/w 3,4-diaminotoluene in 0.1 M K-phosphate, buffer pH 7.0.

Modifiers: 0.1% w/w m-phenylenediamine in 0.1 M K-phosphate buffer, pH 7.0. 0.1% w/w 2,4-diaminoanisole in 0,1 M K-phosphate buffer, pH 7.0. 0.1% w/w alpha-naphthol in 0.1 M K-phosphate buffer, pH 7.0. 0.1% w/w hydroquinone in 0.1 M K-phosphate buffer, pH 7.0. 0.1% w/w pyrocatechol in 0.1 M K-phosphate buffer, pH 7.0. 0.1% w/w resorcinol in 0.1 M K-phosphate buffer, pH 7.0. 0.1% w/w 4-chlororesorcinol in 0.1 M K-phosphate buffer, pH 7.0.

The dye precursor is combined with one of the above indicated modifiers so that the final concentration in the dyeing solution is 0.1% w/w with respect to precursor and 0.1% w/w with respect to modifier.

Other solutions:

Commercial shampoo

Equipment: Minolta CR200 Chroma Meter

Determination of Laccase Activity (LACU)

Laccase activity is determined from the oxidation of syrin-galdazin under aerobic conditions. The violet colour produced is photometered at 530 nm. The analytical conditions are 19 mM syringaldazin, 23.2 mM acetate buffer, pH 5.5, 30° C., 1 min. Reaction time. 1 laccase unit (LACU) is the amount of enzyme that catalyses the conversion of 1.0 micromole syringaldazin per minute at these conditions.

Assessment of the hair colour

The quantitative colour of the hair tresses is determined on a Minolta CR200 Chroma Meter by the use the parameters L* ("0"=black and "100"=white), a* ("−"=green and "+"=red) and b* ("−" blue and "+" yellow).

$\Delta L^*$, $\Delta a^*$ and $\Delta b^*$ are the delta values of L*, a* and b* respectively compared to L*, a* and b* of untreated hair (e.g. $\Delta L^* = L^*_{sample} - L^*_{untreated\ hair}$).

ΔE* is calculated as $\Delta E^* = \sqrt{(\Delta L^{*2} + \Delta a^{*2} + \Delta b^{*2})}$ and is an expression for the total quantitative colour change.

EXAMPLES

Example 1

Dyeing effect

The dyeing effect of different laccases were tested and compared under the same conditions using 0.1% w/w o-aminophenol (dye precursor) and 0.1% w/w m-phenylene-diamine (modifier).

The laccases tested were
a *Polyporus pinsitus* laccase,
a *Myceliophthora thermophila* laccase
a *Myceliophthora thermophila* T1 laccase variant,
a *Rhus vernicifera* laccase
a *Rhizoctonia solani* laccase
a *Scytalidium thermophila* laccase Hair dyeing 1 gram white De Meo hair tresses were used.

4 ml dye precursor solution (including modifier) was mixed with 1 ml laccase on a Whirley mixer, applied to the hair tresses and incubated at 30° C. for 60 minutes.

The hair tresses were then rinsed with running water, washed with shampoo, rinsed with water, combed, and air dried.

a*, b* and L* were determined on the Chroma Meter and ΔE* was then calculated.

Hair tress samples treated without enzyme were used as a blind.

The result of the test is displayed in FIG. 1.

Example 2

Wash stability

Tresses of white De Meo hair (1 gram) were used for testing of the wash stability of hair dyed using the *Myceliophthora thermophila* T-variant laccase and the *Polyporus pinsitus* laccase.

Oxidative hair dyeing was carried out as described in Example 1, except that p-phenylene-diamine (pPD) were used as the dye precursor and no modifiers were used.

Hair wash

The dyed hair tresses were wetted and washed for 15 seconds with 50 ml of commercial shampoo, and rinsed with water for 1 minute and air dried. The hair tresses were washed up to 18 times.

Then a*, b* and L* were determined on the Chroma Meter and ΔE* values were then calculated.

Hair tress samples treated without enzymes were used as blinds.

Figure 2:
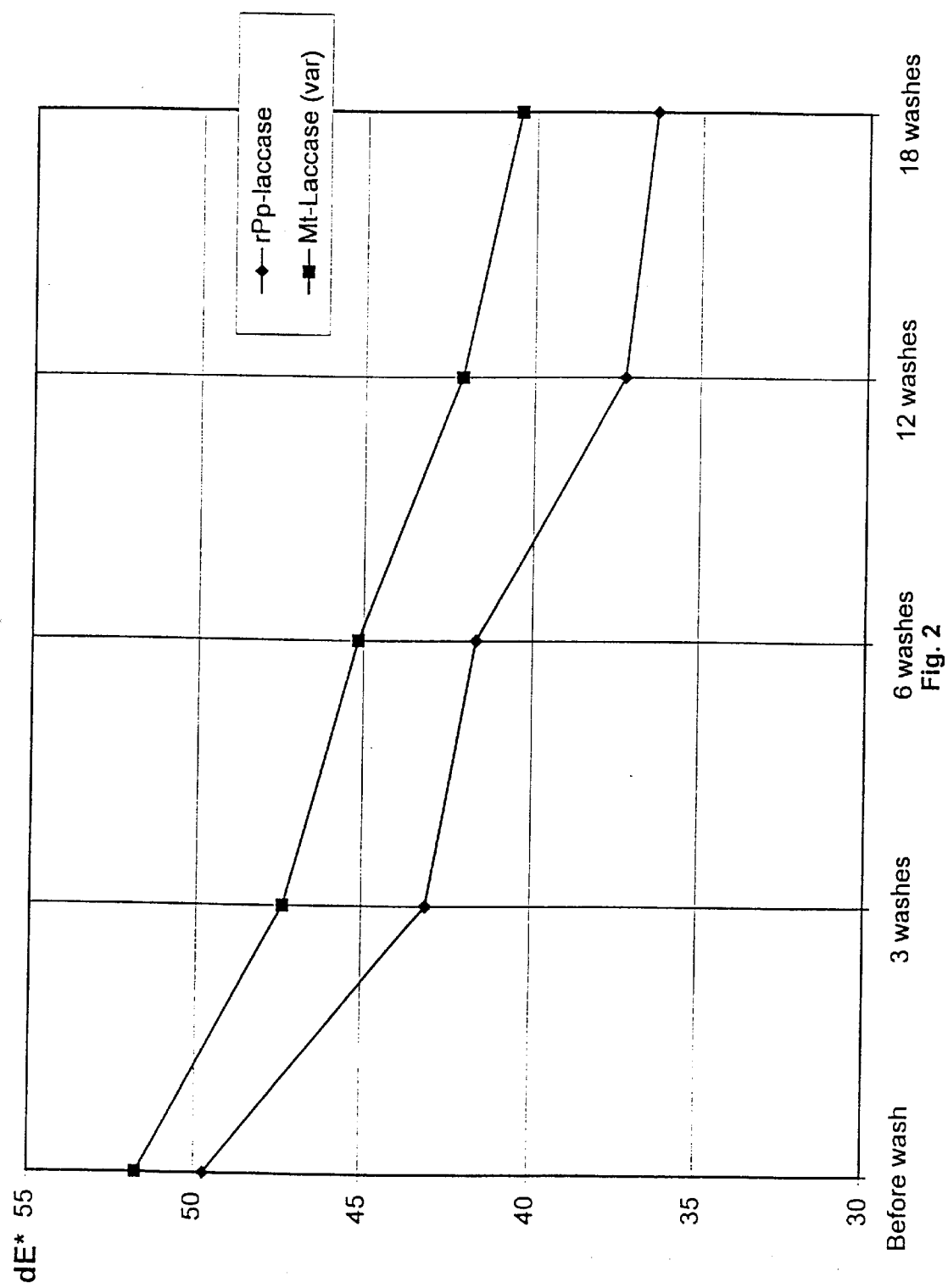
FIG. 2 shows the wash stability of the *Myceliophthora thermophila* T1 variant laccase (Mt-laccase (var)) and the *Polyporus pinsitus* laccase (rPp-laccase) as the oxidising agent.

The result of the test is displayed in FIG. 2.

Example 3

Fastness of hair dyeing

Tresses of white De Meo hair (1 gram) were used for testing fastness (speed) of hair dyeing using the *Myceliophthora thermophila* T1 variant laccase and the *Polyporus pinsitus* laccase.

p-phenylene-diamine (pPD) was used as the dye precursor and no modifiers were used.

4 ml dye precursor solution was mixed with 1 ml laccase on a Whirley mixer, applied to the hair tresses and incubated at 30° C. for 10, 20, 30, 40, 50 and 60 minutes, respectively.

The hair tresses were then rinsed with running water, washed with shampoo, rinsed with running water, combed, and air dried.

a*, b* and L* were determined on the Chroma Meter for each incubation time and the ΔE*-values were then calculated.

Hair tress samples treated without enzymes for 60 minutes were used as blinds.

Figure 3:
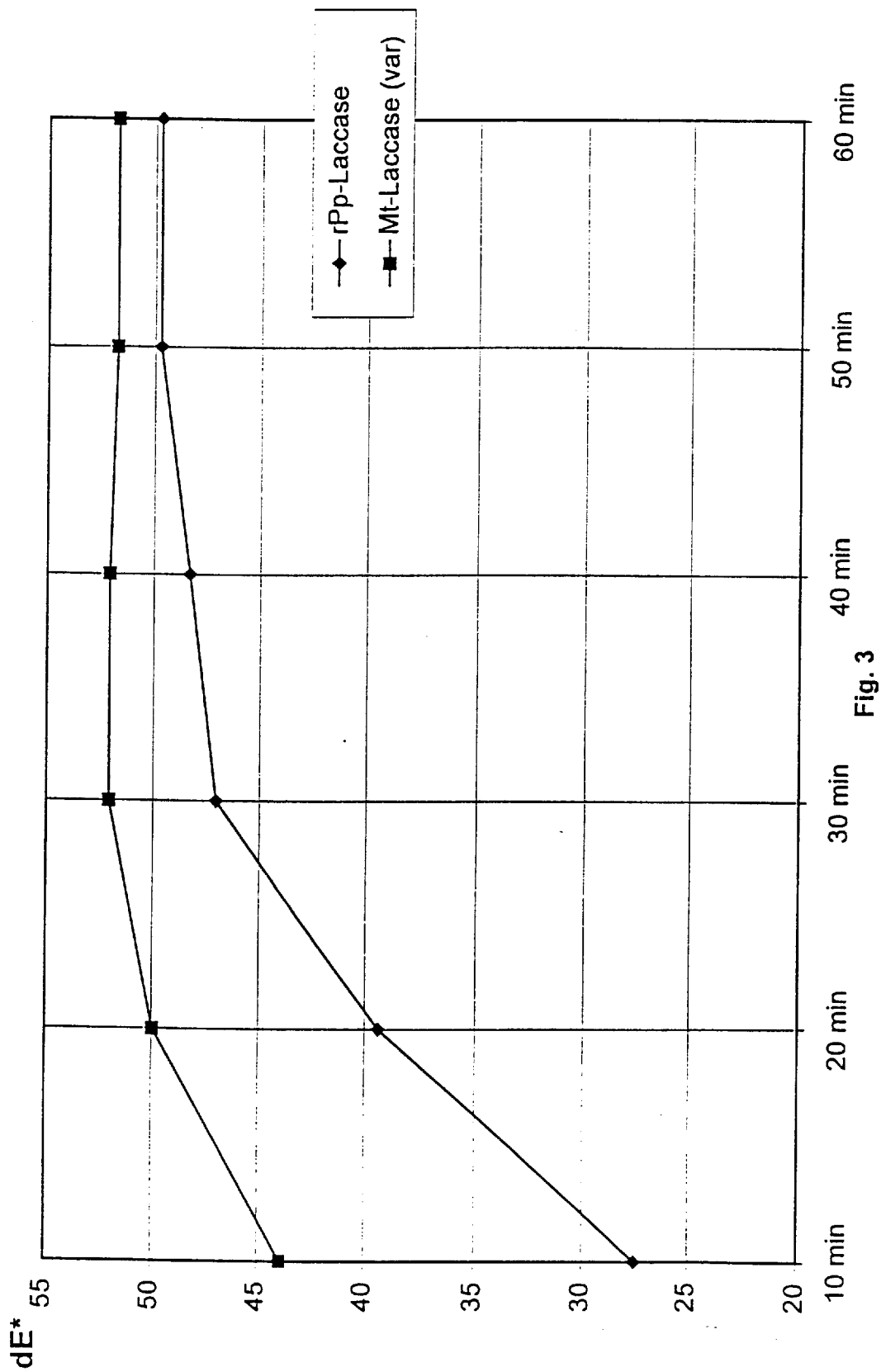
FIG. 3 shows the fastness (speed) of hair dyeing using the *Myceliophthora thermophila* T1 variant laccase (Mt-laccase (var)) and the *Polyporus pinsitus* laccase (rPp-laccase) as the oxidising agent.

The result of the test is displayed in FIG. 3.

Example 4

Dyeing effect of *Myceliophthora thermophila* T1 variant laccase

The dyeing effect of *Myceliophthora thermophila* T1 variant laccase were compared with the *Polyporus pinsitus* laccase using 0.1% w/w p-phenylene-diamine, 0.1% w/w p-touylene-diamine, 0.1% w/w chloro-p-phenylene-diamine, 0.1% w/w p-aminophenol, 0.1% w/w o-aminophenol and 0.1% w/w 3,4 diaminotoluene, respectively, as dye precursors.

The *Polyporus pinsitus* laccase were applied in a concentration of 10 LACU/ml while the *Myceliophthora thermophila* T1 variant laccase was applied in a concentration of only 1 LACU/ml.

1 gram white De Meo hair tresses were used.

4 ml dye precursor solution was mixed with 1 ml laccase on a Whirley mixer, applied to the hair tresses and incubated at 30° C. for 60 minutes.

The hair tresses were then rinsed with running water, washed with shampoo, rinsed with running water, combed, and air dried.

The a*, b* and L* were determined on the Chroma Meter and the ΔE* values were then calculated.

Hair tress samples treated without enzyme were used as blinds.

The result of the test is displayed in Table 1.

TABLE 1

| Sample | Polyporus pinsitus laccase ΔE* | Myceliophthora thermophila T1 variant laccase ΔE* |
|---|---|---|
| p-phenylene-diamine blind | 9.7 | 10.9 |
| p-phenylene-diamine + laccase | 52.7 | 52.9 |
| p-toluylene-diamine blind | 16.1 | 18.6 |
| p-toluylene-diamine + laccase | 39.1 | 38.2 |
| chloro-p-phenylene-diamine blind | 2.6 | 4.0 |
| chloro-p-phenylene-diamine + laccase | 40.5 | 39.2 |
| p-aminophenol blind | 6.2 | 7.0 |
| p-aminophenol + laccase | 32.4 | 28.1 |
| o-amonophenol blind | 5.6 | 6.4 |
| o-amonophenol + laccase | 22.9 | 22.0 |
| 3,4-diaminotoluene blind | 3.4 | 2.6 |
| 3,4-diaminotoluene + laccase | 36.5 | 42.2 |

As can be seen from Table 1 compositions comprising the *Myceliophthora thermophila* T1laccase variant dyes the hair as good as the *Polyporus pinsitus* laccase even though concentration of the *Polyporus pinsitus* laccase is 10 time higher.

Example 5

Dose-response dyeing effect of *M. thermophila* laccase

The dyeing effect of *M. thermophila* laccase were tested using concentration between 0.0001 to 0.5 mg enzyme protein per ml dyeing composition of laccase. 0.1% w/w p-toluylene-diamine (PTD) was used as the dye precursor.

The same dyeing procedure as described in Example 1 was used.

Figure 4:
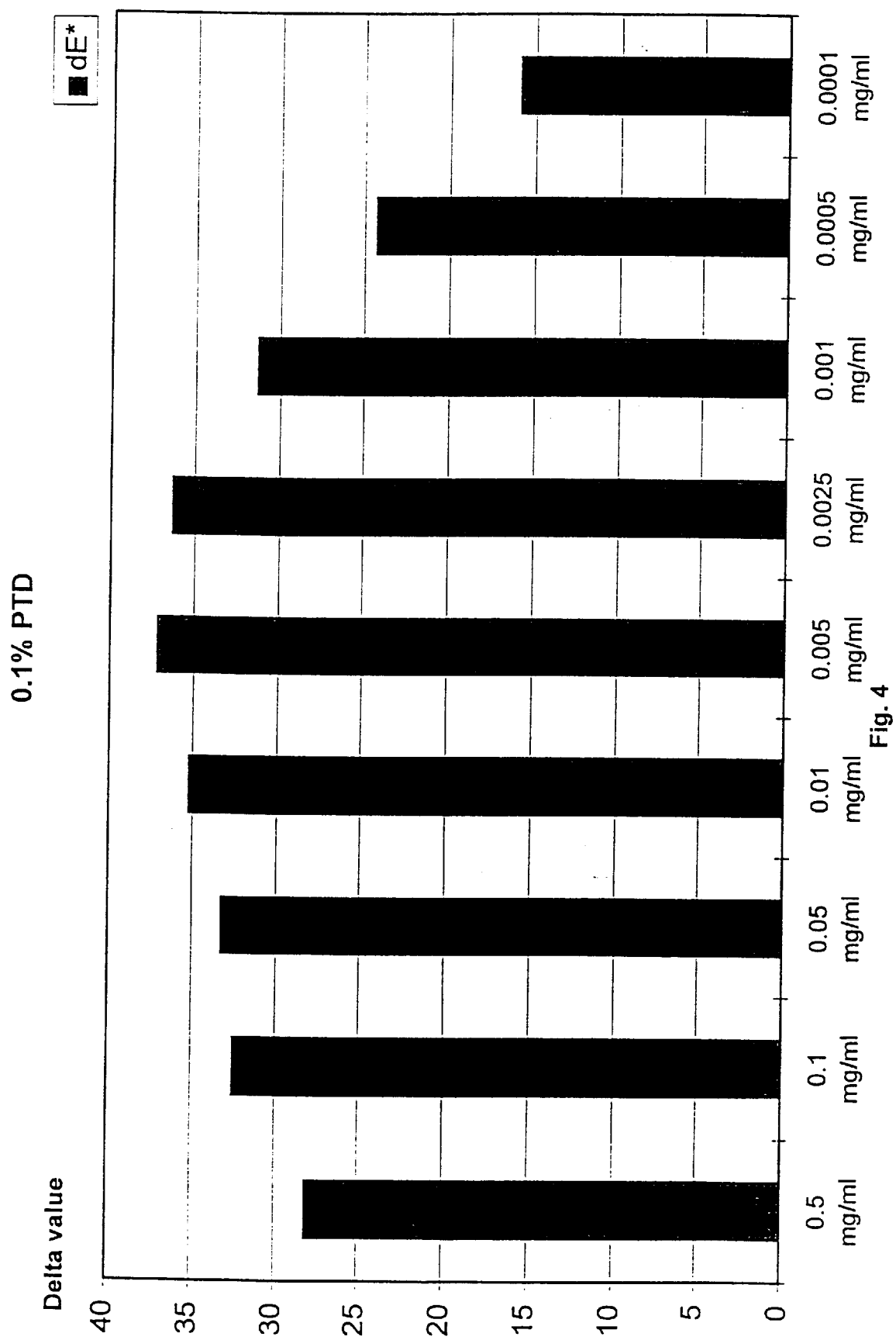
FIG. 4 shows the dose-response dyeing effect of *Myceliophthora thermophila* laccase, using from 0.0001 to 0.5 mg enzyme protein per ml dyeing compoisiton.

The result of the tests are displayed in FIG. 4.

We claim:

1. A dyeing composition comprising
   a) above 0 to 0.1 mg enzyme protein per ml dyeing composition of microbial laccase derived from a strain of the genus Myceliophthora, and
   b) one or more dye precursor(s).

2. The dyeing composition of claim 1, wherein the Myceliophthora laccase is derived from a strain of species *Myceliophthora thermophila* or variants thereof.

3. The dyeing composition of claim 2, wherein the laccase is encoded by the sequence of SEQ ID No: 1.

4. The dyeing composition of claim 2, wherein the Myceliophthora laccase is derived from a strain of *Myceliophthora thermophila* NRRL B 21261 or variants thereof.

5. The dyeing composition of claim 4, wherein the *Myceliophthora thermoplila* NRRL B-21261 laccase variant is a T1 variant.

6. The dyeing composition of claim 1, wherein the dye precursor is selected from the group consisting of p-phenylene-diamine (pPD), p-toluylene-diamine (pTD), chloro-p-phenylenediamine, p-aminophenol, o-aminophenol, 3,4-diamino-toluene, 2-methyl-1,4-diaminobenzene, 4-methyl-o-phenylenediamine, 2-methoxy-p-phenylenediamine, 2-chloro-1,4-diamino-benzene, 4-amino diphenylamine, 1-amino-4-β-methoxyethylamino-benzene, 1-amino-4-bis-(β-hydroxyethyl)-aminobenzene, 1-3-diamino-benzene, 2-methyl-1,3-diamino-benzene, 2,4-diaminotoluene, 2,6-diaminopyridine, 1-hydroxy-2-amino-benzene, 1-hydroxy-3-amino-benzene, 1-methyl-2-hydroxy-4-amino-benzene, 1-methyl-2-hydroxy-4-β-hydroxyethylamino-benzene, 1-hydroxy-4-amino-benzene, 1-hydroxy-4-methylamino-benzene, 1-methoxy-2,4-diamino-benzene, 1-ethoxy2,3-diamino-benzene, 1-β-hydroxyethyloxy-2,4-diamino-benzene, phenazines, 3-amino-7-(dimethylamino)-2,8-dimethyl-5-phenyl-chloride, p-amino benzoic acids, acetylsalicylic acid, and isatin derivatives.

7. The dyeing composition of claim 1 further comprising one or more dye modifier(s).

8. The dyeing composition of claim 7, wherein the dye modifier is selected from the group consisting of m-phenylene-diamine, 2,4-diaminoanisole, 1-hydroxynaphthalene (α-naphthol), 1,4-dihydroxybenzene (hydroquinone), 1,5-dihydroxy-napthalene, 1,2-dihydroxybenzene(pyrocatechol), 1,3-dihydro-xybenzene (resorcinol), 1,3-dihydroxy-2-methylbenzene, 1,3-dihydroxy-4-chlorobenzene (4-chlororesorcinol), 1,2,3,-trihydro-xy-benzene, 1,2,4-trihydroxybenzene, 1,2,4-trihydroxy-5-methyl-benzene, and 1,2,4-trihydroxytoluene.

9. A method for dyeing keratinous fibers comprising contacting the dyeing composition of claim 1 to the keratinous fibers under suitable conditions and for a period of time sufficient to permit oxidation of the dye precursor into a colored compound.

10. The method of claim 9, wherein the dyeing procedure is carried out at a pH in the range from 3 to 10.

11. The method of claim 9, wherein the procedure is carried out for a period of time between 10 and 60 minutes.

12. The method of claim 9, wherein the contacting step is carried out at a pH in the range from 5 to 9.

13. The method of claim 9, wherein the contacting step is carried out at a pH in the range from 6 to 8.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 3192 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: CDS
       (B) LOCATION: join(586..831, 917..994, 1079..1090, 1193..1264,
           1337..2308, 2456..2524, 2618..3028)

(xi) SEQUENCE DESCRIPTION: SEQ ID NO:1:

```
TCTAGCTTCT TTGGTCACCG TCGTTTTCGC CCGCCCCCTC CCTCCTTCAA CCCCCTGAGT      60

AGTCGGCTAA GCGATCCTCA ATCTGGTCTT GTGAGGTCAC GTCCTCCAGC AGATGACAGT     120

TCATCGAGCG AGTGATCTCC ACCACCCAGA AGGGAGGGGG GATGCGCGCA TGCTCCAACA     180

TCCCTGGTGT CGCTAGAGAC GTCGCGGCAT CAGCCTTTTC ATCACACCGA GCACGTCCAC     240

GGACCGGCTC CTTTCACCCC CGCGTCCTCC GGAGGATTGA GTCACGATAT TTCGGGATGT     300

GGGAAGGGGG AGAGAAAGGA GGGGGGAGGG GCGGAAACAT GTTGGATACG AGCTGCGCCC     360

CTTTTTCAAC ATCGAGAACA GGAAGTCGTT GGTGTCGGCC GTAATGTCTA TAAAACGAGG     420

CTCCTTCTCG TCGTCGACTT GTCTCAGGTT CTCTCTCTCG TCCACACCAA GCCAGTCTTG     480

CCTGAGCCAC CTGAGCCACC TTCAACTCAT CATCTTCAGT CAAGTCGTTC ATTGACATTG     540

TGTCTCTCTT TCTATCGAGT CGGCTTCCCG GCCCTTCACC ACAAC ATG AAG TCC         594
                                                 Met Lys Ser
                                                   1

TTC ATC AGC GCC GCG ACG CTT TTG GTG GGC ATT CTC ACC CCT AGC GTT      642
Phe Ile Ser Ala Ala Thr Leu Leu Val Gly Ile Leu Thr Pro Ser Val
  5                  10                  15

GCT GCT GCC CCT CCA TCC ACC CCT GAG CAG CGC GAC CTG CTC GTC CCG      690
Ala Ala Ala Pro Pro Ser Thr Pro Glu Gln Arg Asp Leu Leu Val Pro
 20                  25                  30                  35

ATC ACG GAG AGG GAG GAG GCA GCC GTG AAG GCT CGC CAG CAG AGC TGC      738
Ile Thr Glu Arg Glu Glu Ala Ala Val Lys Ala Arg Gln Gln Ser Cys
                 40                  45                  50

AAC ACC CCC AGC AAC CGG GCG TGC TGG ACT GAC GGA TAC GAC ATC AAC      786
Asn Thr Pro Ser Asn Arg Ala Cys Trp Thr Asp Gly Tyr Asp Ile Asn
             55                  60                  65

ACC GAC TAC GAA GTG GAC AGC CCG GAC ACG GGT GTT GTT CGG CCG          831
Thr Asp Tyr Glu Val Asp Ser Pro Asp Thr Gly Val Val Arg Pro
         70                  75                  80

GTGAGTGCTC TCGTTAATTA CGCTTCGGCG AGTTGCGCAG ATATATTAAA TACTGCAAAC     891

CTAAGCAGGA GCTGACATGC GACAG TAC ACT CTG ACT CTC ACC GAA GTC GAC      943
                             Tyr Thr Leu Thr Leu Thr Glu Val Asp
                                              85                  90

AAC TGG ACC GGA CCT GAT GGC GTC GTC AAG GAG AAG GTC ATG CTG GTT      991
Asn Trp Thr Gly Pro Asp Gly Val Val Lys Glu Lys Val Met Leu Val
                 95                 100                 105

AAC GTACGGCACC CCTTTTCTTG TCCTAGGATC TGGGTGATGT GCGTCGTTGC           1044
Asn
```

-continued

```
CCCTGAGAGA GACTGACCGA GCCTTTGGCT GCAG AAT AGT ATA ATC GTAATTAATT        1100
                                      Asn Ser Ile Ile
                                              110

ATACCGCCCT GCCTCCAGCA GCCCCAGCAG CTCGAGAAGG GTATCTGAAG TTAGTCAGGC       1160

CTGCTGACCT GACCGGGGCC AACCCACCAT AG GGA CCA ACA ATC TTT GCG GAC         1213
                                    Gly Pro Thr Ile Phe Ala Asp
                                                    115

TGG GGC GAC ACG ATC CAG GTA ACG GTC ATC AAC AAC CTC GAG ACC AAC         1261
Trp Gly Asp Thr Ile Gln Val Thr Val Ile Asn Asn Leu Glu Thr Asn
120             125             130             135

GGC GTATGTCTGC TGCTTGCTCT CTTGCTCTCC TCGTCCGCGA CTAATAATAA              1314
Gly

TATCAACTCG TGTGGAAAAC AG ACG TCG ATC CAC TGG CAC GGA CTG CAC CAG        1366
                        Thr Ser Ile His Trp His Gly Leu His Gln
                                        140             145

AAG GGC ACC AAC CTG CAC GAC GGC GCC AAC GGT ATC ACC GAG TGC CCG         1414
Lys Gly Thr Asn Leu His Asp Gly Ala Asn Gly Ile Thr Glu Cys Pro
        150             155             160

ATC CCG CCC AAG GGA GGG AGG AAG GTG TAC CGG TTC AAG GCT CAG CAG         1462
Ile Pro Pro Lys Gly Gly Arg Lys Val Tyr Arg Phe Lys Ala Gln Gln
        165             170             175

TAC GGG ACG AGC TGG TAC CAC TCG CAC TTC TCG GCC CAG TAC GGC AAC         1510
Tyr Gly Thr Ser Trp Tyr His Ser His Phe Ser Ala Gln Tyr Gly Asn
180             185             190

GGC GTG GTC GGG GCC ATT CAG ATC AAC GGG CCG GCC TCG CTG CCG TAC         1558
Gly Val Val Gly Ala Ile Gln Ile Asn Gly Pro Ala Ser Leu Pro Tyr
195             200             205             210

GAC ACC GAC CTG GGC GTG TTC CCC ATC AGC GAC TAC TAC TAC AGC TCG         1606
Asp Thr Asp Leu Gly Val Phe Pro Ile Ser Asp Tyr Tyr Tyr Ser Ser
                215             220             225

GCC GAC GAG CTG GTG GAA CTC ACC AAG AAC TCG GGC GCG CCC TTC AGC         1654
Ala Asp Glu Leu Val Glu Leu Thr Lys Asn Ser Gly Ala Pro Phe Ser
                230             235             240

GAC AAC GTC CTG TTC AAC GGC ACG GCC AAG CAC CCG GAG ACG GGC GAG         1702
Asp Asn Val Leu Phe Asn Gly Thr Ala Lys His Pro Glu Thr Gly Glu
        245             250             255

GGC GAG TAC GCC AAC GTG ACG CTC ACC CCG GGC CGG CGG CAC CGC CTG         1750
Gly Glu Tyr Ala Asn Val Thr Leu Thr Pro Gly Arg Arg His Arg Leu
260             265             270

CGC CTG ATC AAC ACG TCG GTC GAG AAC CAC TTC CAG GTC TCG CTC GTC         1798
Arg Leu Ile Asn Thr Ser Val Glu Asn His Phe Gln Val Ser Leu Val
275             280             285             290

AAC CAC ACC ATG ACC ATC ATC GCC GCC GAC ATG GTG CCC GTC AAC GCC         1846
Asn His Thr Met Thr Ile Ile Ala Ala Asp Met Val Pro Val Asn Ala
                295             300             305

ATG ACG GTC GAC AGC CTC TTC CTC GGC GTC GGC CAG CGC TAC GAT GTC         1894
Met Thr Val Asp Ser Leu Phe Leu Gly Val Gly Gln Arg Tyr Asp Val
                310             315             320

GTC ATC GAA GCC AGC CGA ACG CCC GGG AAC TAC TGG TTT AAC GTC ACA         1942
Val Ile Glu Ala Ser Arg Thr Pro Gly Asn Tyr Trp Phe Asn Val Thr
        325             330             335

TTT GGC GGC GGC CTG CTC TGC GGC GGC TCC AGG AAT CCC TAC CCG GCC         1990
Phe Gly Gly Gly Leu Leu Cys Gly Gly Ser Arg Asn Pro Tyr Pro Ala
        340             345             350

GCC ATC TTC CAC TAC GCC GGC GCC CCC GGC GGC CCG CCC ACG GAC GAG         2038
Ala Ile Phe His Tyr Ala Gly Ala Pro Gly Gly Pro Pro Thr Asp Glu
355             360             365             370

GGC AAG GCC CCG GTC GAC CAC AAC TGC CTG GAC CTC CCC AAC CTC AAG         2086
Gly Lys Ala Pro Val Asp His Asn Cys Leu Asp Leu Pro Asn Leu Lys
```

-continued

```
                     375                 380                 385
CCC GTC GTG GCC CGC GAC GTG CCC CTG AGC GGC TTC GCC AAG CGG CCC     2134
Pro Val Val Ala Arg Asp Val Pro Leu Ser Gly Phe Ala Lys Arg Pro
            390                 395                 400

GAC AAC ACG CTC GAC GTC ACC CTC GAC ACC ACG GGC ACG CCC CTG TTC     2182
Asp Asn Thr Leu Asp Val Thr Leu Asp Thr Thr Gly Thr Pro Leu Phe
            405                 410                 415

GTC TGG AAG GTC AAC GGC AGC GCC ATC AAC ATC GAC TGG GGC AGG CCC     2230
Val Trp Lys Val Asn Gly Ser Ala Ile Asn Ile Asp Trp Gly Arg Pro
            420                 425                 430

GTC GTC GAC TAC GTC CTC ACG CAG AAC ACC AGC TTC CCA CCC GGG TAC     2278
Val Val Asp Tyr Val Leu Thr Gln Asn Thr Ser Phe Pro Pro Gly Tyr
435                 440                 445                 450

AAC ATT GTC GAG GTG AAC GGA GCT GAT CAG GTAAGAAAAA GGGGACCGCA       2328
Asn Ile Val Glu Val Asn Gly Ala Asp Gln
                455                 460

GGGGTGCTGC TGCAAGTACA CCTTGCTCGC CCTCCTGTTC TTCCTTAATA ACTACCTCCC   2388

AACCCTCCCC CCTAATTAAT TCACTTTAAA GGCCGATCAA GACTGACCGA GCCCCCTCTC   2448

TTTGCAG TGG TCG TAC TGG TTG ATC GAG AAC GAT CCC GGC GCA CCT TTC    2497
        Trp Ser Tyr Trp Leu Ile Glu Asn Asp Pro Gly Ala Pro Phe
                        465                 470

ACC CTA CCG CAT CCG ATG CAC CTG CAC GTAAGTTGGA TACATATATA           2544
Thr Leu Pro His Pro Met His Leu His
475                 480

TATATATATA TACATTGCTT TCCTGGCTCG CTCCCTTAAA TAAAATTAAA TAACCAAAAA   2604

TAACAAAAAA AAG GGC CAC GAC TTT TAC GTG CTG GGC CGC TCG CCC GAC     2653
            Gly His Asp Phe Tyr Val Leu Gly Arg Ser Pro Asp
                485                 490                 495

GAG TCG CCG GCA TCC AAC GAG CGG CAC GTG TTC GAT CCG GCG CGG GAC     2701
Glu Ser Pro Ala Ser Asn Glu Arg His Val Phe Asp Pro Ala Arg Asp
            500                 505                 510

GCG GGC CTG CTG AGC GGG GCC AAC CCT GTG CGG CGG GAC GTG ACG ATG     2749
Ala Gly Leu Leu Ser Gly Ala Asn Pro Val Arg Arg Asp Val Thr Met
            515                 520                 525

CTG CCG GCG TTC GGG TGG GTG GTG CTG GCC TTC CGG GCC GAC AAC CCG     2797
Leu Pro Ala Phe Gly Trp Val Val Leu Ala Phe Arg Ala Asp Asn Pro
            530                 535                 540

GGC GCC TGG CTG TTC CAC TGC CAC ATC GCC TGG CAC GTC TCG GGC GGC     2845
Gly Ala Trp Leu Phe His Cys His Ile Ala Trp His Val Ser Gly Gly
545                 550                 555

CTG GGC GTC GTC TAC CTC GAG CGC GCC GAC GAC CTG CGC GGG GCC GTC     2893
Leu Gly Val Val Tyr Leu Glu Arg Ala Asp Asp Leu Arg Gly Ala Val
560                 565                 570                 575

TCG GAC GCC GAC GCC GAC GAC CTC GAC CGC CTC TGC GCC GAC TGG CGC     2941
Ser Asp Ala Asp Ala Asp Asp Leu Asp Arg Leu Cys Ala Asp Trp Arg
            580                 585                 590

CGC TAC TGG CCT ACC AAC CCC TAC CCC AAG TCC GAC TCG GGC CTC AAG     2989
Arg Tyr Trp Pro Thr Asn Pro Tyr Pro Lys Ser Asp Ser Gly Leu Lys
            595                 600                 605

CAC CGC TGG GTC GAG GAG GGC GAG TGG CTG GTC AAG GCG TGAGCGAAGG      3038
His Arg Trp Val Glu Glu Gly Glu Trp Leu Val Lys Ala
            610                 615                 620

AGGAAAAAGG AAACAAAGAG GGGGGGGGGG GCTAGTTCCT ATTTTTGCTT TTTTTTTTTG   3098

TTCTTGTCCT TGTGCTGGCG GTTACCCTGG TAAAGGAGAA GGGGGCCCCA AGTTCGAGTG   3158

GGTGTGTGAT CGGGTAAATA TTATCAAGAG ATCT                              3192
```

(2) INFORMATION FOR SEQ ID NO:2:

(i) SEQUENCE CHARACTERISTICS:
    (A) LENGTH: 620 amino acids
    (B) TYPE: amino acid
    (D) TOPOLOGY: linear (ii) MOLECULE TYPE: protein (xi) SEQUENCE DESCRIPTION: SEQ ID NO:2:

```
Met Lys Ser Phe Ile Ser Ala Ala Thr Leu Leu Val Gly Ile Leu Thr
 1               5                  10                  15

Pro Ser Val Ala Ala Pro Pro Ser Thr Pro Glu Gln Arg Asp Leu
            20                  25                  30

Leu Val Pro Ile Thr Glu Arg Glu Ala Ala Val Lys Ala Arg Gln
            35                  40                  45

Gln Ser Cys Asn Thr Pro Ser Asn Arg Ala Cys Trp Thr Asp Gly Tyr
 50                  55                  60

Asp Ile Asn Thr Asp Tyr Glu Val Asp Ser Pro Asp Thr Gly Val Val
 65                  70                  75                  80

Arg Pro Tyr Thr Leu Thr Leu Thr Glu Val Asp Asn Trp Thr Gly Pro
            85                  90                  95

Asp Gly Val Val Lys Glu Lys Val Met Leu Val Asn Asn Ser Ile Ile
            100                 105                 110

Gly Pro Thr Ile Phe Ala Asp Trp Gly Asp Thr Ile Gln Val Thr Val
            115                 120                 125

Ile Asn Asn Leu Glu Thr Asn Gly Thr Ser Ile His Trp His Gly Leu
 130                 135                 140

His Gln Lys Gly Thr Asn Leu His Asp Gly Ala Asn Gly Ile Thr Glu
145                 150                 155                 160

Cys Pro Ile Pro Pro Lys Gly Gly Arg Lys Val Tyr Arg Phe Lys Ala
                165                 170                 175

Gln Gln Tyr Gly Thr Ser Trp Tyr His Ser His Phe Ser Ala Gln Tyr
            180                 185                 190

Gly Asn Gly Val Val Gly Ala Ile Gln Ile Asn Gly Pro Ala Ser Leu
            195                 200                 205

Pro Tyr Asp Thr Asp Leu Gly Val Phe Pro Ile Ser Asp Tyr Tyr Tyr
210                 215                 220

Ser Ser Ala Asp Glu Leu Val Glu Leu Thr Lys Asn Ser Gly Ala Pro
225                 230                 235                 240

Phe Ser Asp Asn Val Leu Phe Asn Gly Thr Ala Lys His Pro Glu Thr
                245                 250                 255

Gly Glu Gly Glu Tyr Ala Asn Val Thr Leu Thr Pro Gly Arg Arg His
            260                 265                 270

Arg Leu Arg Leu Ile Asn Thr Ser Val Glu Asn His Phe Gln Val Ser
            275                 280                 285

Leu Val Asn His Thr Met Thr Ile Ile Ala Ala Asp Met Val Pro Val
            290                 295                 300

Asn Ala Met Thr Val Asp Ser Leu Phe Leu Gly Val Gly Gln Arg Tyr
305                 310                 315                 320

Asp Val Val Ile Glu Ala Ser Arg Thr Pro Gly Asn Tyr Trp Phe Asn
                325                 330                 335

Val Thr Phe Gly Gly Leu Leu Cys Gly Gly Ser Arg Asn Pro Tyr
            340                 345                 350

Pro Ala Ala Ile Phe His Tyr Ala Gly Ala Pro Gly Gly Pro Pro Thr
            355                 360                 365

Asp Glu Gly Lys Ala Pro Val Asp His Asn Cys Leu Asp Leu Pro Asn
```

-continued

```
                370              375              380
Leu Lys Pro Val Val Ala Arg Asp Val Pro Leu Ser Gly Phe Ala Lys
385                  390              395                  400

Arg Pro Asp Asn Thr Leu Asp Val Thr Leu Asp Thr Thr Gly Thr Pro
                405              410              415

Leu Phe Val Trp Lys Val Asn Gly Ser Ala Ile Asn Ile Asp Trp Gly
                420              425              430

Arg Pro Val Val Asp Tyr Val Leu Thr Gln Asn Thr Ser Phe Pro Pro
            435              440              445

Gly Tyr Asn Ile Val Glu Val Asn Gly Ala Asp Gln Trp Ser Tyr Trp
            450              455              460

Leu Ile Glu Asn Asp Pro Gly Ala Pro Phe Thr Leu Pro His Pro Met
465              470              475              480

His Leu His Gly His Asp Phe Tyr Val Leu Gly Arg Ser Pro Asp Glu
                485              490              495

Ser Pro Ala Ser Asn Glu Arg His Val Phe Asp Pro Ala Arg Asp Ala
            500              505              510

Gly Leu Leu Ser Gly Ala Asn Pro Val Arg Arg Asp Val Thr Met Leu
            515              520              525

Pro Ala Phe Gly Trp Val Val Leu Ala Phe Arg Ala Asp Asn Pro Gly
            530              535              540

Ala Trp Leu Phe His Cys His Ile Ala Trp His Val Ser Gly Gly Leu
545              550              555              560

Gly Val Val Tyr Leu Glu Arg Ala Asp Asp Leu Arg Gly Ala Val Ser
                565              570              575

Asp Ala Asp Ala Asp Asp Leu Asp Arg Leu Cys Ala Asp Trp Arg Arg
            580              585              590

Tyr Trp Pro Thr Asn Pro Tyr Pro Lys Ser Asp Ser Gly Leu Lys His
        595              600              605

Arg Trp Val Glu Glu Gly Glu Trp Leu Val Lys Ala
        610              615              620
```